United States Patent
Charania et al.

(10) Patent No.: US 9,507,916 B2
(45) Date of Patent: Nov. 29, 2016

(54) CONTAINER FOR ACCURATELY DISPENSING MEDICATION

(71) Applicant: Cellco Partnership, Basking Ridge, NJ (US)

(72) Inventors: Rahim A. Charania, Euless, TX (US); Alex Hoyos, Miami, FL (US); Kevin Lim, Danville, CA (US)

(73) Assignee: Cellco Partnership, Basking Ridge, NJ (US)

( * ) Notice: Subject to any disclaimer, the term of this patent is extended or adjusted under 35 U.S.C. 154(b) by 130 days.

(21) Appl. No.: 14/228,869

(22) Filed: Mar. 28, 2014

(65) Prior Publication Data
US 2015/0278478 A1 Oct. 1, 2015

(51) Int. Cl.
G06F 19/00 (2011.01)
A61J 7/04 (2006.01)

(52) U.S. Cl.
CPC ............ *G06F 19/3462* (2013.01); *A61J 7/049* (2015.05); *A61J 7/0418* (2015.05); *A61J 7/0436* (2015.05); *A61J 7/0445* (2015.05); *A61J 7/0454* (2015.05); *A61J 7/0481* (2013.01); *A61J 2205/30* (2013.01)

(58) Field of Classification Search
CPC ............ G06F 19/3462; G06F 19/3468; A61J 7/0481; A61J 7/0445; A61J 7/0436; A61J 7/0418; A61J 7/0454; A61J 7/049; A61J 2205/30
USPC ................................................ 700/231–244
See application file for complete search history.

(56) References Cited

U.S. PATENT DOCUMENTS

| | | | | |
|---|---|---|---|---|
| 5,042,685 A * | 8/1991 | Moulding, Jr. ....... | A61J 7/0409 | 221/1 |
| 5,646,912 A * | 7/1997 | Cousin ................. | A61J 7/0481 | 221/15 |
| 6,194,995 B1 * | 2/2001 | Gates ................... | A61J 7/0481 | 206/531 |
| 6,249,717 B1 * | 6/2001 | Nicholson ............ | A61J 7/0481 | 222/246 |
| 6,294,999 B1 * | 9/2001 | Yarin .................... | A61J 7/0481 | 340/573.1 |
| 6,529,446 B1 * | 3/2003 | de la Huerga ....... | A61J 7/0084 | 368/10 |
| 7,359,765 B2 * | 4/2008 | Varvarelis ............ | A61J 7/0481 | 221/265 |
| 8,752,728 B2 * | 6/2014 | Tignanelli ............ | A61J 1/03 | 221/15 |
| 2007/0170199 A1 * | 7/2007 | York .................... | A61J 7/0481 | 221/150 R |
| 2009/0294521 A1 * | 12/2009 | de la Huerga ......... | A61J 1/035 | 235/375 |
| 2010/0164716 A1 * | 7/2010 | Estevez ................ | A61J 7/0481 | 340/540 |
| 2010/0283601 A1 * | 11/2010 | Tai ....................... | G06Q 50/24 | 340/539.12 |
| 2011/0163843 A1 * | 7/2011 | Vallone ............... | G06F 19/3462 | 340/5.3 |
| 2011/0166698 A1 * | 7/2011 | Vallone ............... | G06F 19/3462 | 700/233 |
| 2013/0035785 A1 * | 2/2013 | MacVittie .......... | B65D 83/0409 | 700/231 |

(Continued)

OTHER PUBLICATIONS

SMRxT, Inc., "SMRxT Realtime Medication Adherence", SMRxT, Inc., Aug. 9, 2013, 3 pages.

(Continued)

*Primary Examiner* — Patrick Cicchino

(57) ABSTRACT

A container may include a secure chamber to hold a medication, a lockable lid that covers an opening of the secure chamber, a dispensing device, and one or more processors. The container may receive prescription information indicating a frequency to dispense the medication and indicating a dose of the medication to dispense at a dispense time. The container may determine the dispense time based on the frequency to dispense the medication. The dispense time may be a time to dispense a dose of the medication. The container may cause the dispensing device to dispense the dose of the medication from the secure chamber at the dispense time.

20 Claims, 11 Drawing Sheets

(56) References Cited

U.S. PATENT DOCUMENTS

2013/0197693 A1* 8/2013 Kamen ............... G06F 19/3462
700/244
2014/0251850 A1* 9/2014 Huang ..................... A61J 1/03
206/459.1

OTHER PUBLICATIONS

SMRxT, Inc., "SMRxT Realtime Medication Adherence", http://www.smrxt.com/index.php., 2012, 2 pages.

* cited by examiner

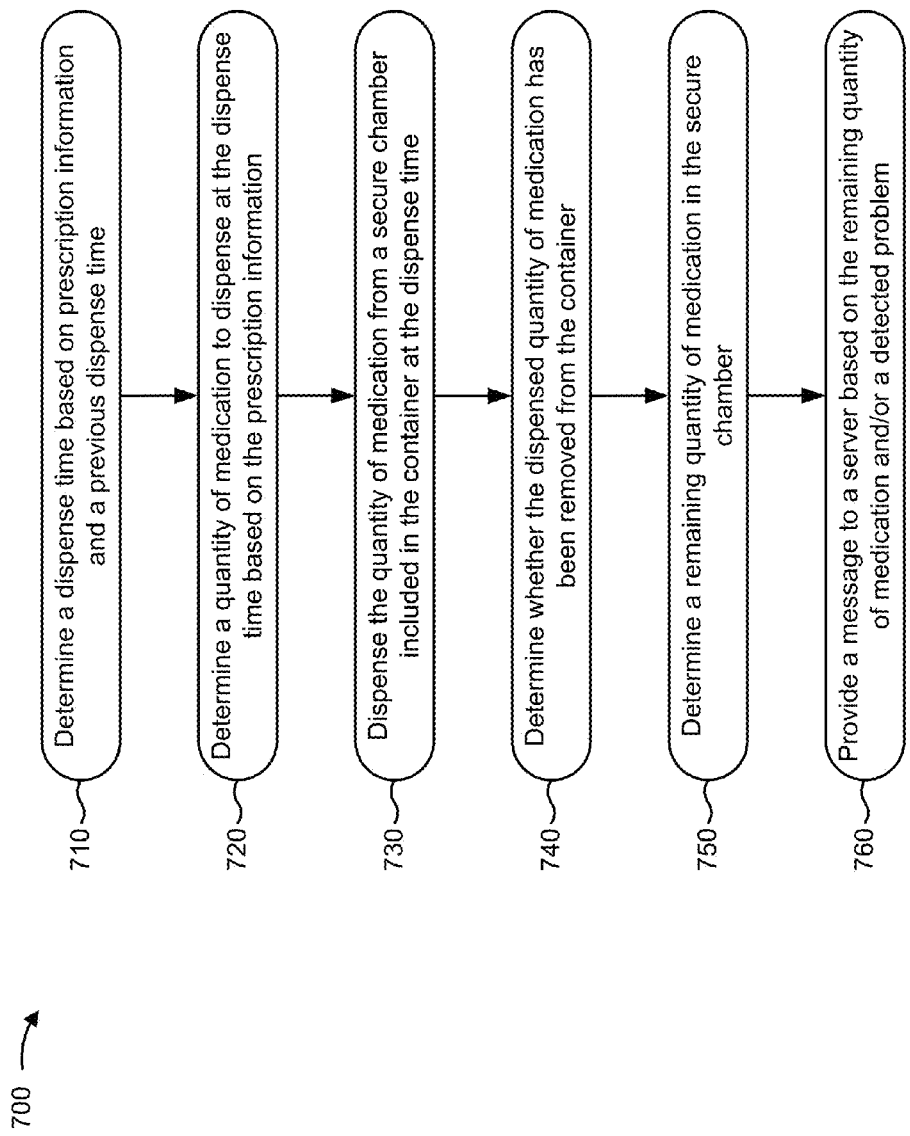

CONTAINER FOR ACCURATELY DISPENSING MEDICATION

BACKGROUND

A prescription bottle contains prescribed medicine and may include a label that provides information about the medicine. For example, the label may indicate how much of the medication should be taken and how often the medication should be taken.

BRIEF DESCRIPTION OF THE DRAWINGS

FIG. 7 is a flow chart of an example process for dispensing medication held by a container;

DETAILED DESCRIPTION OF PREFERRED EMBODIMENTS

The following detailed description of example implementations refers to the accompanying drawings. The same reference numbers in different drawings may identify the same or similar elements.

A patient who keeps medication in a prescription bottle may forget to take the medication at a correct time and/or intentionally or unintentionally take a wrong amount of the medication. Moreover, the patient may not always be able to accurately measure a proper dose of a liquid or cream medication and end up taking too little or too much.

Implementations described herein provide a container that may dispense an accurate amount of medication at prescribed times. Accordingly, the container may help a patient take a prescribed dosage of medication at a prescribed time.

Figure 1:
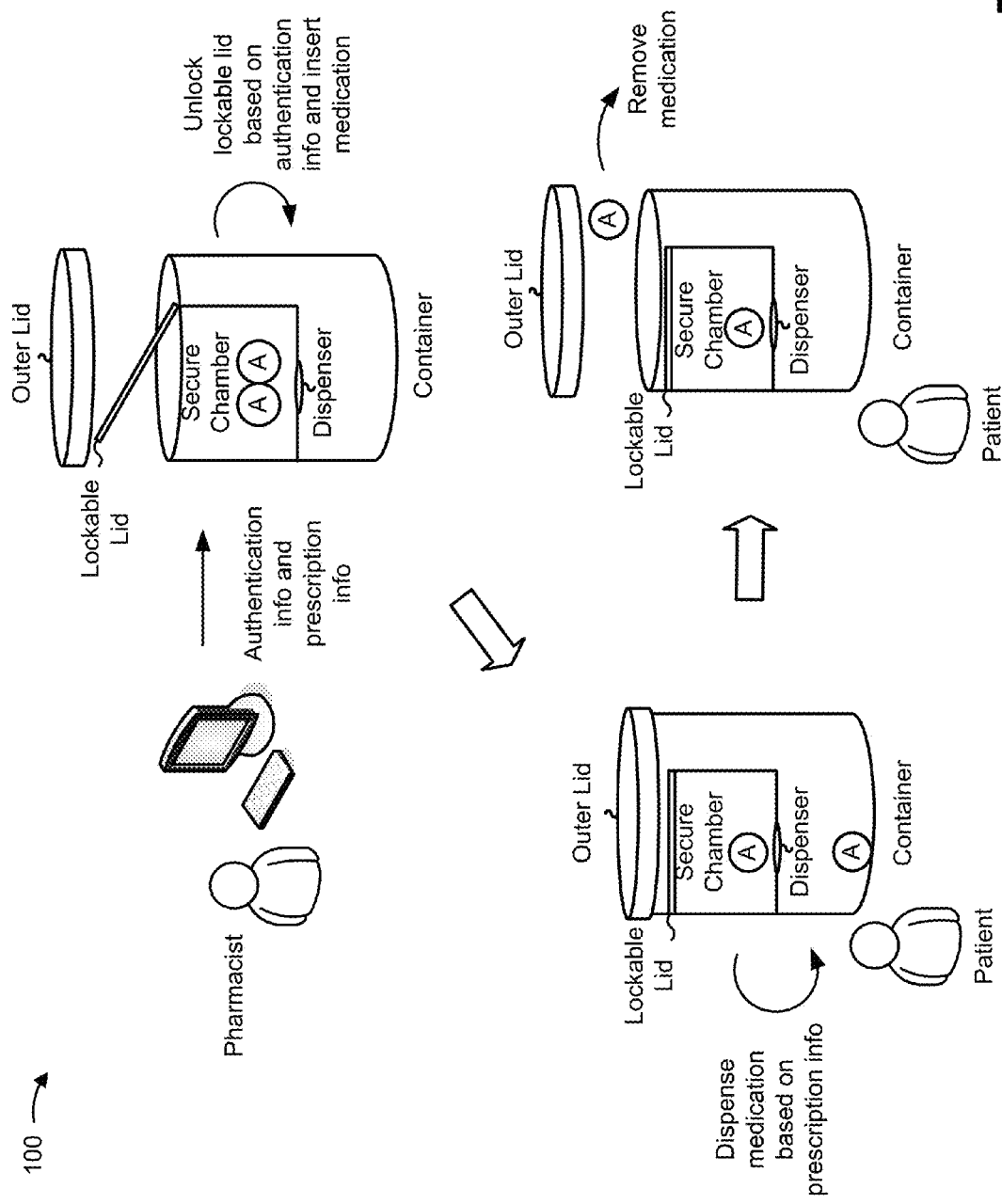
FIG. 1 is a diagram of an overview of an example implementation described herein.

FIG. 1 is a diagram of an overview of an example implementation 100 described herein. In example implementation 100, assume a container includes an outer lid, a secure chamber, a lockable lid that covers the secure chamber, and a dispenser that dispenses medication out of the secure chamber. Further, assume a pharmacist is authorized to unlock the lockable lid.

The pharmacist may input authentication information for unlocking the lid and prescription information associated with a prescription into a user device. Assume the prescription information indicates a dose of medication (e.g., one pill) should be dispensed at a dispense time. The user device may transmit the authentication information and the prescription information to the container.

The container may receive the authentication information and the prescription information. The container may unlock the lockable lid based on the authentication information. The pharmacist may open the outer lid of the container and the lockable lid of the secure container, and insert medication associated with prescription into the secure chamber. The pharmacist may close the lockable lid and the outer lid, and the container may lock the lockable lid. The pharmacist may give the container to a patient.

The container may dispense a dose of the medication (e.g., a pill) at the dispense time indicated by the prescription information. For example, the dispenser may cause a pill to move from the secure chamber to an unlocked portion of the container. The patient may open the outer lid and remove the pill from the unlocked portion of the container.

In this way, the container may dispense an accurate dose of medication (e.g., one pill) at a prescribed dispense time. Although example implementation 100 uses pills as an example of the medication, implementations described herein may apply to other kinds of medication (e.g., fluids, liquids, creams, oils, gels, ointments, etc.).

Figure 2:
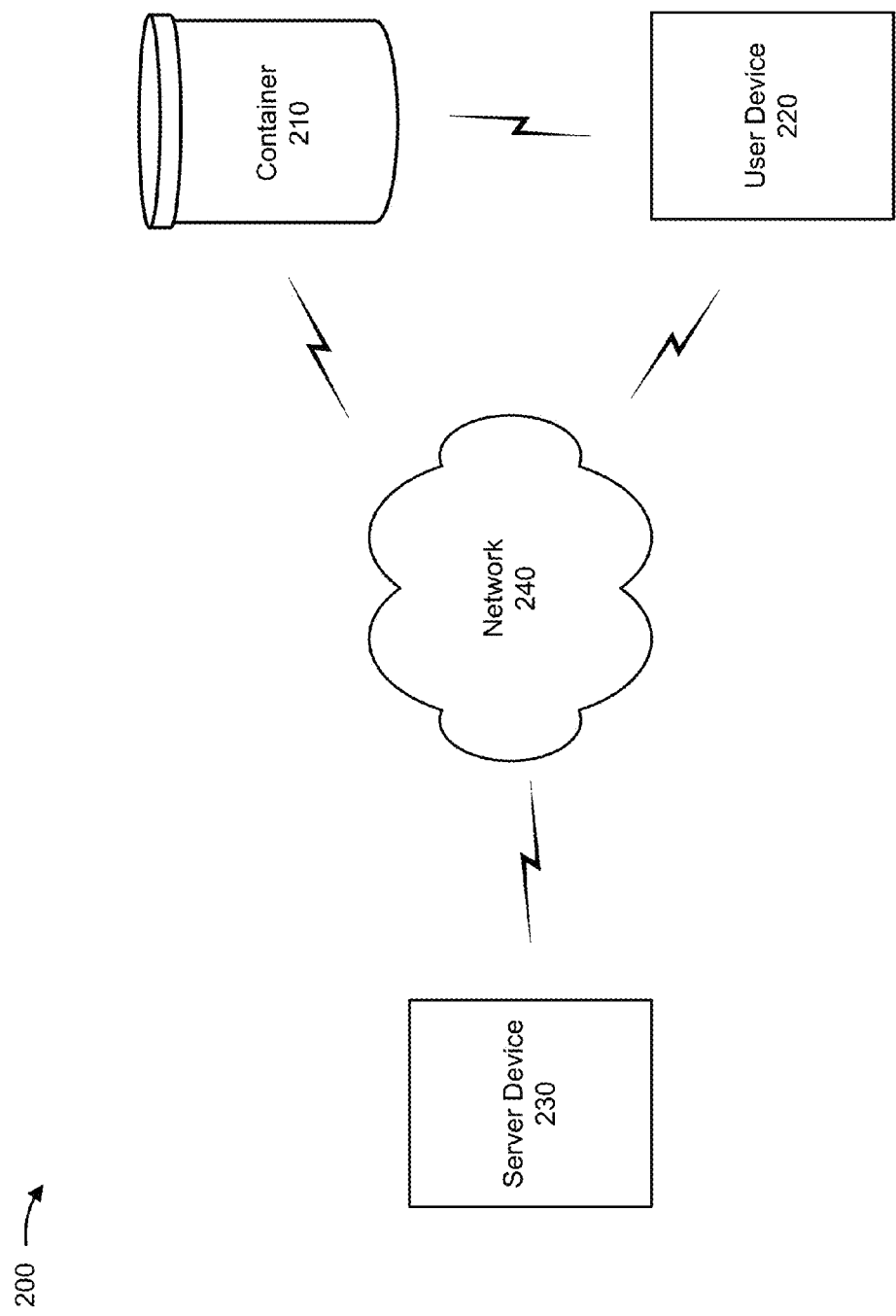
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a container 210, a user device 220, a server device 230, and/or a network 240. Devices of environment 200 may interconnect via wired connections, wireless connections (e.g., Bluetooth, RF connection, etc.), or a combination of wired and wireless connections.

Container 210 may include a device capable of holding medication and capable of receiving, processing, and/or providing information. For example, container 210 may be a bottle, a vessel, a box, and/or another kind of container. In some implementations, container 210 may include a communication interface that allows container 210 to receive information from and/or transmit information to user device 220, server device 230, and/or another device in environment 200.

User device 220 may include a device capable of receiving, processing, and/or providing information. For example, user device 220 may include a mobile phone (e.g., a smart phone, a radiotelephone, etc.), a computing device (e.g., a laptop computer, a tablet computer, a handheld computer, etc.), or a similar device. In some implementations, user device 220 may include a communication interface that allows user device 220 to receive information from and/or transmit information to container 210, server device 230, and/or another device in environment 200. In some implementations, user device 220 may transmit prescription information to container 210.

Server device 230 may include one or more devices capable of processing and/or routing information. In some implementations, server device 230 may include a communication interface that allows server device 230 to receive information from and/or transmit information to other devices in environment 200.

Network 250 may include one or more wired and/or wireless networks. For example, network 250 may include a cellular network, a public land mobile network (PLMN), a local area network (LAN), a wide area network (WAN), a metropolitan area network (MAN), a telephone network (e.g., the Public Switched Telephone Network (PSTN)), an ad hoc network, an intranet, the Internet, a fiber optic-based network, a satellite network, a cloud computing network, and/or a combination of these or other types of networks.

The number and arrangement of devices and networks shown in FIG. 2 is provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
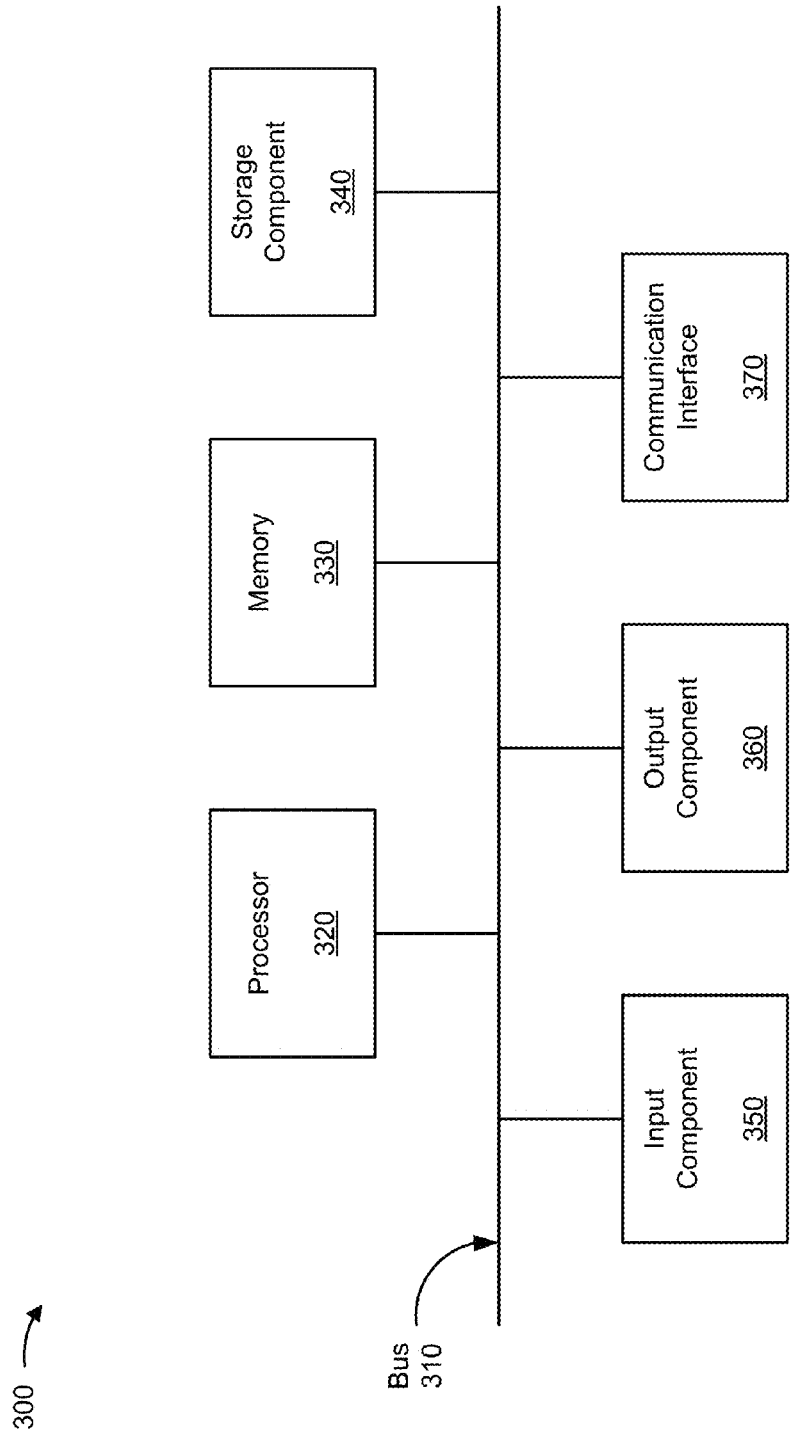
FIG. 3 is a diagram of example components of one or more devices of FIG. 2.

FIG. 3 is a diagram of example components of a device 300. Device 300 may correspond to container 210, user device 220, and/or server device 230. In some implementations, container 210, user device 220, and/or server device 230 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 may include a component that permits communication among the components of device 300. Processor 320 may include a processor (e.g., a central processing unit (CPU), a graphics processing unit (GPU), an accelerated processing unit (APU), etc.), a microprocessor, and/or any processing component (e.g., a field-programmable gate array (FPGA), an application-specific integrated circuit (ASIC), etc.) that interprets and/or executes instructions. Memory 330 may include a random access memory (RAM), a read only memory (ROM), and/or another type of dynamic or static storage device (e.g., a flash memory, a magnetic memory, an optical memory, etc.) that stores information and/or instructions for use by processor 320.

Storage component 340 may store information and/or software related to the operation and use of device 300. For example, storage component 340 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 350 may include a component that permits device 300 to receive information, such as via user input (e.g., a touch screen display, a keyboard, a keypad, a mouse, a button, a switch, a microphone, etc.). Additionally, or alternatively, input component 350 may include a sensor for sensing information (e.g., a global positioning system (GPS) component, an accelerometer, a gyroscope, an actuator, a scale, a volume sensor, etc.). Output component 360 may include a component that provides output information from device 300 (e.g., a display, a speaker, one or more light-emitting diodes (LEDs), etc.).

Communication interface 370 may include a transceiver-like component (e.g., a transceiver, a separate receiver and transmitter, etc.) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes in response to processor 320 executing software instructions stored by a computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 is provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
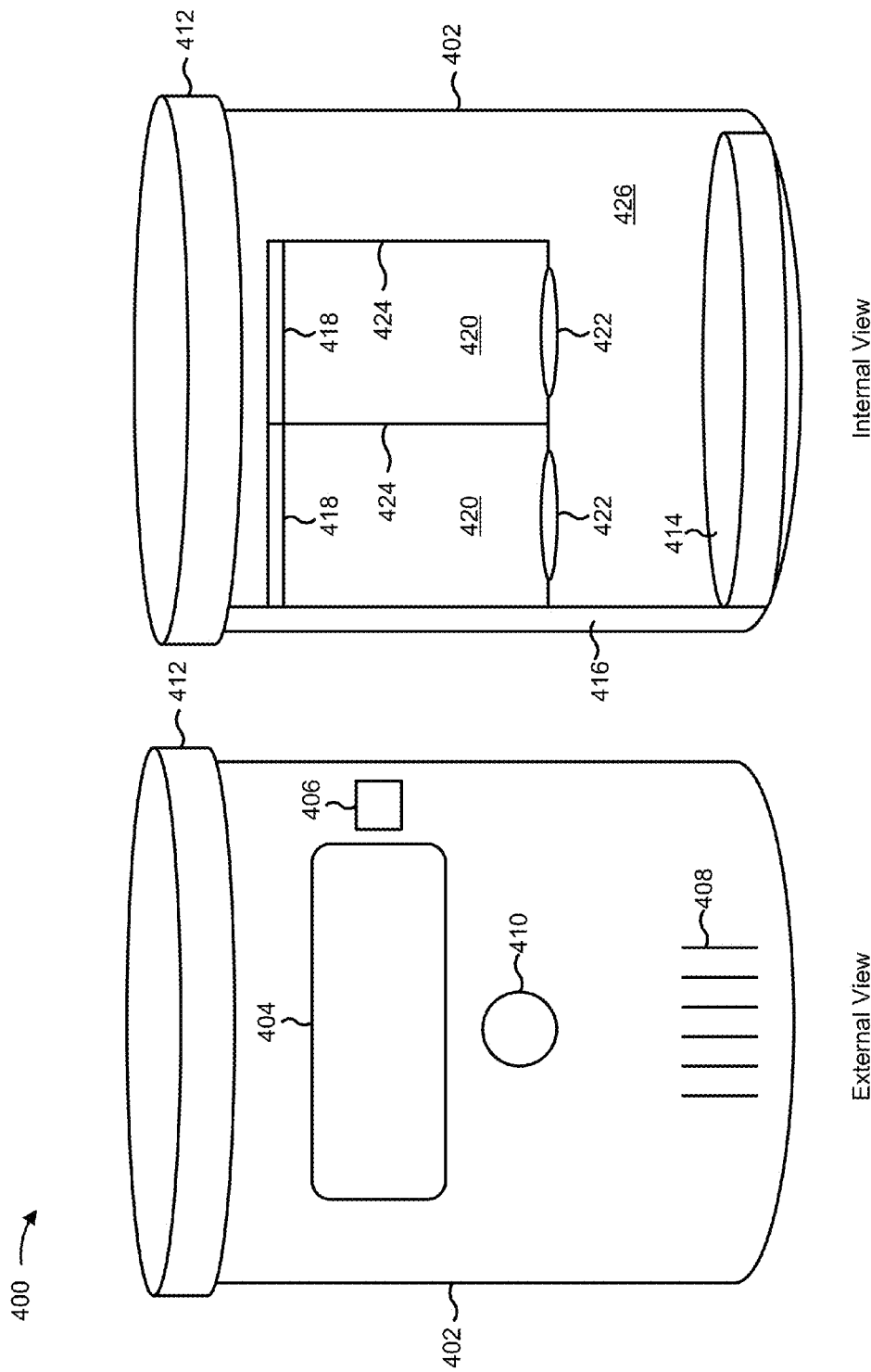
FIG. 4 is a diagram of example components of a pill container corresponding to a container of FIG. 2.

FIG. 4 is a diagram of example components of a pill container 400 corresponding to container 210 of FIG. 2. In other words, pill container 400 may be an example of container 210 that dispenses medication in pill form. FIG. 4 illustrates an internal view and an external view of pill container 400.

As shown in FIG. 4, pill container 400 may include a housing 402, a display 404, an indicator light 406, a speaker 408, a button 410, an outer lid 412, a scale 414, an electronics housing 416, a lockable lid 418, a secure chamber 420, a dispenser 422, an internal housing 424, and/or a dispensing chamber 426.

Housing 402 may include a casing that provides structural support for pill container 400. Housing 402 may be comprised of a plastic material, a metal material, a glass material, and/or another material.

Display 404 may include a LED display, a LCD display, a plasma display, and/or any other kind of display. Display 404 may include a touch screen that allows a user to provide inputs. Indicator light 406 may be any kind of light (e.g., a LED) used output a light. Speaker 408 may be used to output sound. Display 404, indicator light 406, and/or speaker 408 may provide indications to a user. For example, display 404, indicator light 406, and/or speaker 408 may be used to indicate an alert to a user (e.g., medication dispensed, access to medication prohibited, etc.).

Button 410 may be a button that allows a user to provide inputs to pill container 400. Pill container 400 may include one or more buttons 410. Button 410 may be used to silence an alarm, indicate medication was taken, request medication to be dispensed, report a problem with medication being dispensed, turn on or off display 404, input authentication information, etc.

Outer lid 412 may a lid that covers an opening of housing 402. In some implementations, outer lid 412 may cover an opening of dispensing chamber 426 and/or lockable lid 418. Outer lid 412 may be manually opened or closed, and/or manually locked or unlocked. When opened, outer lid 412 may provide a user access to dispensing chamber 426 and/or lockable lid 418. In some implementations, outer lid 412 may be detachable from housing 402. Additionally, or alternatively, outer lid 412 may be attached to housing 402 by a hinge (not shown) or another type of connector. Outer lid 412 may rotate about the hinge when opened. Additionally, or alternatively, outer lid 412 may include a door (not shown) that covers a slot (not shown). The door may rotate about a hinge (not shown) and/or slide to uncover the slot when opened.

Scale 414 may measure a weight of medication inside dispensing chamber 426. Scale 414 may be located on an inside, bottom surface of housing 402. In some implementations, scale 414 may cover the entire inside, bottom surface of housing 402. A top surface of scale 414 may be a bottom surface of dispensing chamber 426. In some implementations, pill container 400 may include more than one scale located on more than one surface and/or more than one portion of the bottom surface of dispensing chamber 426. For example, each inside surface of dispensing chamber 426 and/or an inside surface of outer lid 412 may include a scale 414. Additionally, or alternatively, pill container 400 may include a gyroscope (not shown) used to determine which scale 410 is parallel to the ground and should be used to measure the weight of the medication.

In some implementations, one or more inner surfaces of internal housing 424 and/or lockable lid 418 may include a scale 414 that may measure a weight of medication inside secure chamber 420. In some implementations, scale 414 may be integrated with dispenser 422 to weigh medication and dispense medication.

Electronics housing 416 may include bus 310, processor 320, memory 330, storage component 340, communication interface 370, a battery, and/or connections for input component 350 (e.g., button 404, a touch screen, etc.) and/or output component 360 (e.g., display 404, indicator light 406, speaker 408, etc.). Electronics housing 416 may be included anywhere within pill container 400.

Lockable lid 418 may be a lid that covers an opening of secure chamber 420. In some implementations, lockable lid 418 may be an electromechanical device that may be electronically controlled to lock, unlock, open, and/or close. In some implementations, lockable lid 418 may be manually locked or unlocked (e.g., using a key). When unlocked and opened, lockable lid 418 may be removed from internal housing 424 to provide a user access to secure chamber 420 and medication contained therein. In some implementations, lockable lid 418 may be detachable from internal housing 424 and may be detached to provide access to secure chamber 420. Additionally, or alternatively, lockable lid 418 may be attached to internal housing 424 by a hinge (not shown) or another type of connector. Lockable lid 418 may rotate about the hinge when unlocked to provide a user access to secure chamber 420. Additionally, or alternatively, lockable lid 418 may include a door (not shown) that covers a slot (not shown). The door may rotate about a hinge (not shown) and/or slide to uncover the slot when unlocked and provide access to secure chamber 420.

Secure chamber 420 may be a concave shaped interior portion of internal housing 424 that may hold medication. Lockable lid 418 may cover an opening of and secure access to secure chamber 420. Lockable lid 418 may be moved to uncover the opening and provide a user access to secure chamber 420. Pill container 400 may include one or more secure chambers 420.

Dispenser 422 may by an electromechanical device that dispenses medication (e.g., one or more pills) from secure chamber 420 into dispensing chamber 426. In some implementations, dispenser 422 may control a number of pills dispensed from secure chamber 420 into dispensing chamber 426 at any one time. In some implementations, dispenser 422 may include a rim that surrounds an opening big enough to hold one pill. In some implementation's, the size and/or shape of the opening may be configurable by a processor (e.g., processor 320) included in pill container 400. For example, the processor may send a signal to dispenser 422 to change the size and/or shape of the rim surrounding the opening to change the size and/or shape of the opening. In some implementations, the size and/or shape of the opening may be set based on the size and/or shape of pills included in secure chamber 420. In some implementations, dispenser 422 may include a top cover between the opening and secure chamber 420. The top cover may open to allow a pill in secure chamber 420 to fall into the opening. The top cover may then close securing one pill in the opening. Dispenser 422 may include a bottom cover between the opening and dispensing chamber 426. The bottom cover may open to allow the pill to fall into dispensing chamber 426. The bottom cover may then close. Additionally, or alternatively, the opening may be included in a wheel that is configured to rotate between a space that allows the pill to fall into the opening from secure chamber 420 and a space that allows the pill to fall into dispensing chamber 426 from the opening.

Internal housing 424 may include a casing that surrounds secure chamber 420. Housing 402 may be comprised of a plastic material, a metal material, a glass material, and/or another material.

Dispensing chamber 426 may be a concave shaped interior portion of housing 402 that may hold medication. Outer lid 412 may cover an opening of dispensing chamber 426. Outer lid 412 may be moved to uncover the opening and provide a user access to medication held by dispensing chamber 426.

The number and arrangement of components shown in FIG. 4 is provided as an example. In practice, pill container 400 may include differently arranged components than those shown in FIG. 4. For example, outer lid 412 may not cover lockable lid 418, and lockable lid 418 may be on an external surface of housing 402. In other words, lockable lid 418 may be accessed by a user without having to open outer lid 412. In some implementations, pill container 400 may include additional components, fewer components, and/or different components than those shown in FIG. 4. For example, FIG. 4 illustrates pill container 400 having two lockable lids 418, two secure chambers 420, two dispensers 422, and two inner housings 424. However, pill container 400 may include more than or fewer than two lockable lids 418, two secure chambers 420, two dispensers 422, and/or two inner housings 424.

Figure 5:
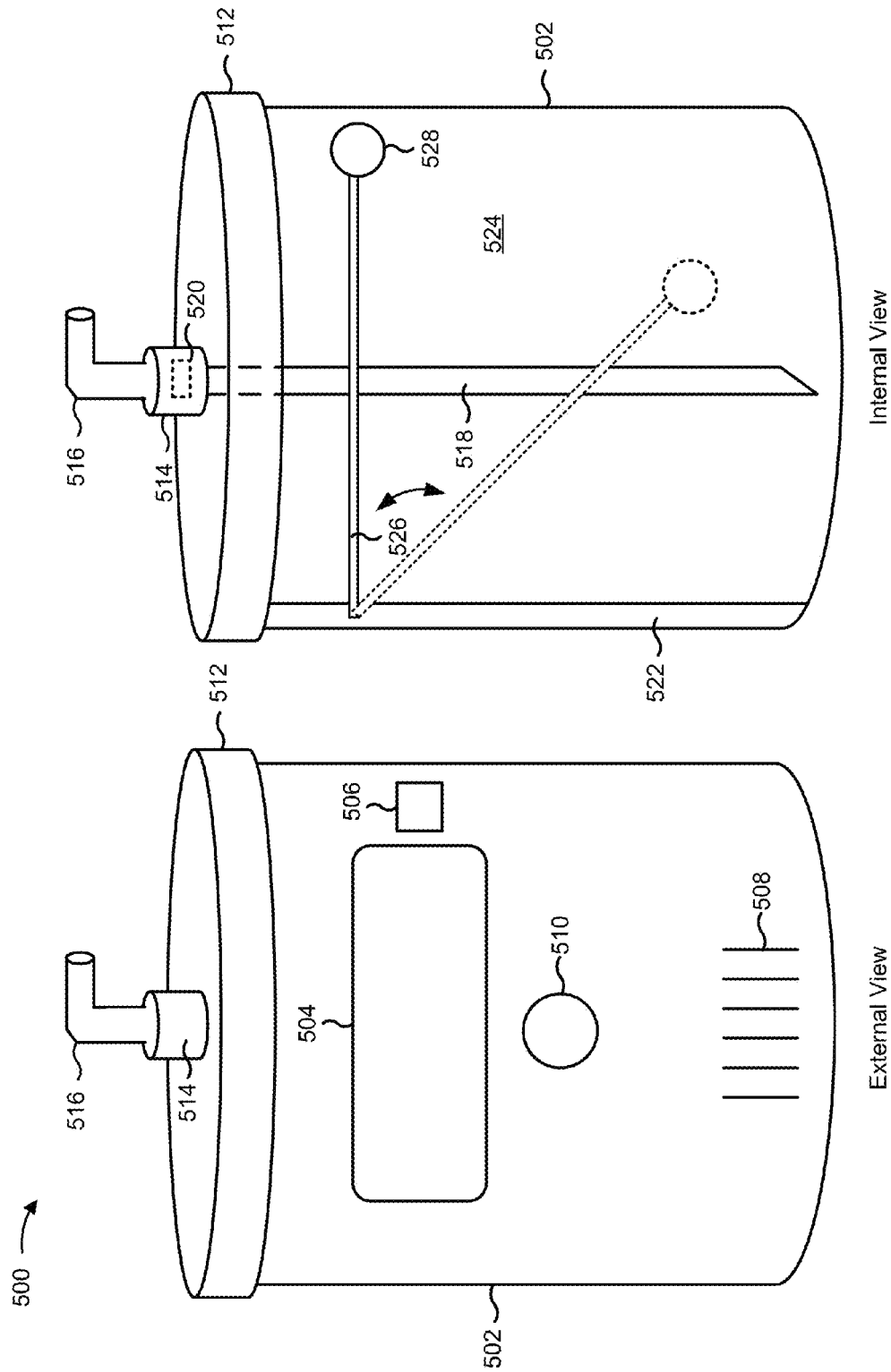
FIG. 5 is a diagram of example components of a fluid container corresponding to a container of FIG. 2.

FIG. 5 is a diagram of example components of a fluid container 500 corresponding to container 210 of FIG. 2. In other words, fluid container 500 may be an example of container 210 that dispenses medication in fluid form (e.g., a liquid, a cream, an oil, a gel, an ointment, etc.). FIG. 5 illustrates an internal view and an external view of fluid container 500.

As shown in FIG. 5, fluid container 500 may include a housing 502, a display 504, an indicator light 506, a speaker 508, a button 510, a lockable lid 512, a pump 514, a nozzle 516, a tube 518, a sensor 520, an electronics housing 522, a secure chamber 524, a rod 526, and/or a float 528.

Housing 502 may include a casing that provides structural support for fluid container 500. Housing 502 may be comprised of a plastic material, a metal material, a glass material, and/or another material.

Display 504 may include a LED display, a LCD display, a plasma display, and/or any other kind of display. Display 504 may include a touch screen that allows a user to provide inputs. Indicator light 506 may be any kind of light (e.g., a LED) used output a light. Speaker 508 may be used to output sound. Display 504, indicator light 506, and/or speaker 508 may provide indications to a user. For example, display 504, indicator light 506, and/or speaker 508 may be used to indicate an alert to a user (e.g., medication dispensed, access to medication prohibited, etc.).

Button 510 may be a button that allows a user to provide inputs to fluid container 500. Fluid container 500 may include one or more buttons 510. Button 510 may be used to silence an alarm, indicate medication was taken, control dispensing of medication, report a problem with medication being dispensed, turn on or off display 504, input authentication information, etc.

Lockable lid 512 may be a lid that covers an opening of secure chamber 524. In some implementations, lockable lid 512 may be an electromechanical device that may be electronically controlled to lock, unlock, open, and/or close. Additionally, or alternatively, lockable lid 512 may be manually locked or unlocked (e.g., using a key). In some implementations, lockable lid 512 may be detachable from housing 502 and may be detached to provide access to secure chamber 524. Additionally, or alternatively, lockable lid 512 may be attached to housing 502 by a hinge (not shown) or another type of connector. Lockable lid 512 may rotate about the hinge when unlocked to provide a user access to secure chamber 524. Additionally, or alternatively, lockable lid 512 may include a door (not shown) that covers a slot (not shown). The door may rotate about a hinge (not shown) and/or slide to uncover the slot when unlocked and provide access to secure chamber 524.

Pump 514 may be used to pump medication held by secure chamber 524 up tube 518 and out of nozzle 516. Pump 514 may be an electromechanical device that automatically pumps the medication. Additionally, or alternatively, pump 514 may be a manual pump that requires a user to depress nozzle 516 to pump the medication. Pump 514 may be configured to control a quantity of medication that is pumped by pump 514. Nozzle 516 may include an opening out of which medication may be pumped. Tube 518 may include an opening through which medication is pumped from secure chamber 524. Sensor 520 may include a sensor to detect a quantity of medication pumped by pump 514 and dispensed through nozzle 516.

Electronics housing 522 may include bus 310, processor 320, memory 330, storage component 340, communication interface 370, a battery, and/or connections for input component 350 (e.g., button 510, a touch screen, etc.) and/or output component 360 (e.g., display 504, indicator light 506, speaker 508, etc.). Electronics housing 522 may be included anywhere in fluid container 500.

Secure chamber 524 may be a concave shaped interior portion of housing 502 that may hold medication. Lockable lid 512 may cover an opening of secure chamber 524. Lockable lid 512 may be moved to uncover the opening and provide a user access to secure chamber 524.

Rod 526 and float 528 may act as a sensor for detecting a volume of medication held by secure chamber 524. Rod 526 may be attached to float 528 at one end. The other end of rod 526 may pivot allowing float 528 to move up and down. Float 528 may be made of a material that allows float 528 to float on the surface of a fluid medication held by secure chamber 524. Rod 526 and float 528 may be used to detect an amount of medication held by secure chamber 524.

For example, rod 526 may include a conductive material on one end that slides along a variable resistor (not shown) and changes a resistance based on the orientation of rod 526 to the variable resistor. The amount of resistance may be used to determine the volume of fluid medication held by secure chamber 524. Additionally, or alternatively, a scale (not shown) (e.g., scale 414) may be placed at the bottom of secure chamber 524 that measures a weight of the medication held by secure chamber 524. A quantity of medication remaining in secure chamber 524 may be determined based on the weight measured by the scale.

The number and arrangement of components shown in FIG. 5 is provided as an example. In practice, fluid container 500 may include differently arranged components than those shown in FIG. 5. In some implementations, fluid container 500 may include additional components, fewer components, and/or different components than those shown in FIG. 5. For example, FIG. 5 illustrates fluid container 500 including one secure chamber 524. However, fluid container 500 may include more than one secure chamber 524, each having a respective pump 514, nozzle 516, tube 518, sensor 520, rod 526, and/or float 528. Additionally, or alternatively, fluid container 500 may include an upper dispensing chamber (not shown) above lockable lid 512. Nozzle 516 may dispense the medication into the upper dispensing chamber. The upper dispensing chamber may be covered by an outer lid (e.g., outer lid 412) that may be opened and/or removed to provide access to the dispensed medication held by the upper dispensing chamber.

Figure 6:
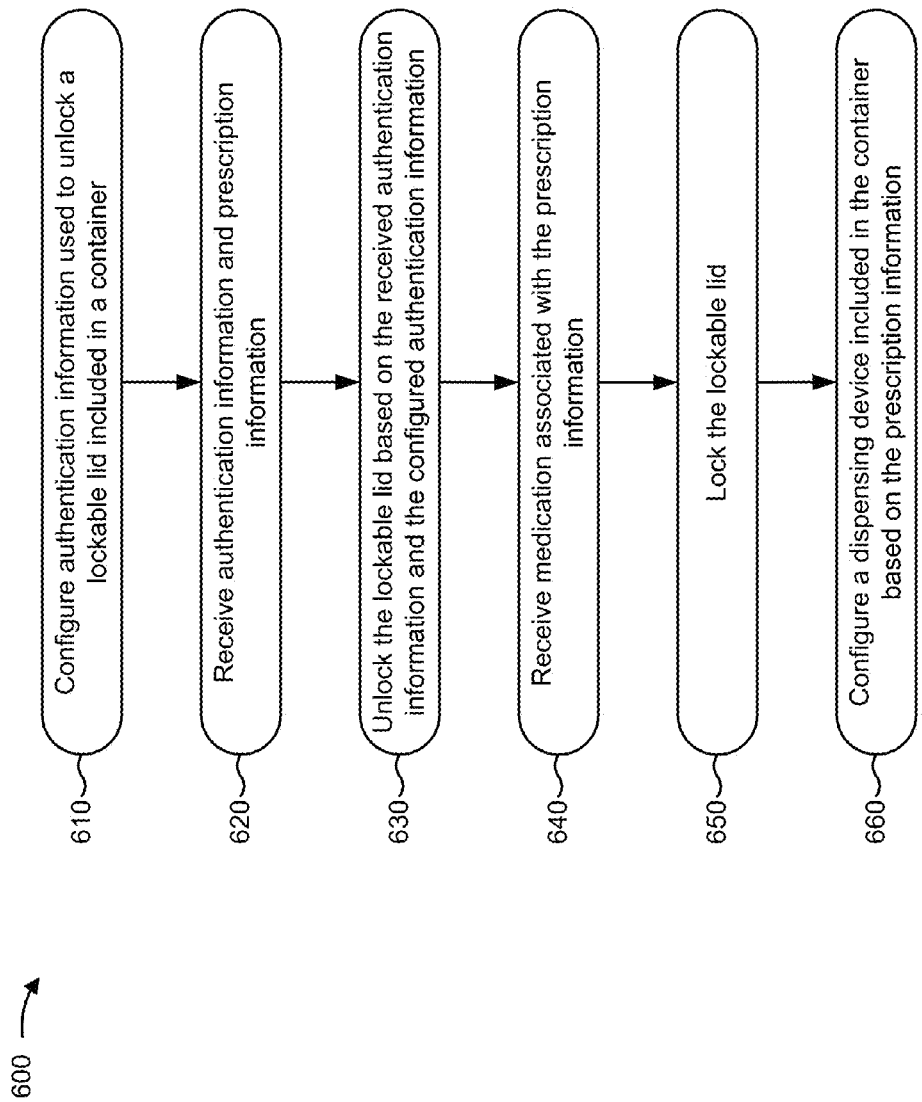
FIG. 6 is a flow chart of an example process for inserting medication into a container.

FIG. 6 is a flow chart of an example process 600 for inserting medication into container 210. In some implementations, one or more process blocks of FIG. 6 may be performed by container 210. In some implementations, one or more process blocks of FIG. 6 may be performed by another device or a group of devices separate from or including container 210, such as user device 220 and/or server device 230.

As used herein, the term "container 210" may refer to pill container 400, fluid container 500, and/or a similar type of container.

As shown in FIG. 6, process 600 may include configuring authentication information used to unlock a lockable lid included in container 210 (block 610). For example, container 210 may configure authentication information used to unlock a lockable lid included in container 210 (e.g., lockable lid 418 and/or lockable lid 512).

User device 220 and/or server device 230 may send authentication information to container 210. Container 210 may receive the authentication information from user device 220 and/or server device 230. The authentication information may be used to authenticate that a user is permitted to unlock the lockable lid. For example, the authentication information may be a password, a personal identification number (PIN), a random string of characters, etc. In some implementations, an authenticated user may be a pharmacist and/or a medical professional that fills prescriptions and inserts medication into container 210. Container 210 may store the authentication information in a memory included in container 210.

In some implementations, the authentication information may be updated and/or reconfigured each time container 210 is used to fill a prescription.

A lockable lid (e.g., lockable lid 418 and/or lockable lid 512) included in container 210 may be locked after the authentication information is configured (e.g., received and stored).

As further shown in FIG. 6, process 600 may include receiving authentication information and prescription information (block 620). For example, container 210 may receive the authentication information and the prescription information.

A user (e.g., a pharmacist) may desire to insert medication into container 210 to fill a prescription. The user may input the authentication information and the prescription information into user device 220. User device 220 may send the authentication information and the prescription information to container 210 and container 210 may receive the authentication information and the prescription information. In some implementations, container 210 may receive the authentication information and/or the prescription information from user device 220 via network 240. In some implementations, container 210 may receive the authentication information and/or the prescription information directly from user device 220. For example, user device 220 may use Bluetooth, Near Field Communication (NFC), and/or RF communication to send the authentication information and/or the prescription information to container 210. Furthermore, user device 220 may connect to container 210 via a wired interface to send the authentication information and/or the prescription information to container 210 (e.g., via a USB connection). Additionally, or alternatively, a user may input the authentication information and/or the prescription information into container 210 via input components (e.g., input component 350, button 410, button 510, a touchscreen, etc.) included in container 210.

The prescription information may identify a medication name, a dosage of the medication (e.g., a quantity of pills, a quantity of fluid, etc.), a weight of the dosage of medication (e.g., a weight of a pill, a weight of a quantity of fluid, etc.), a quantity of total doses of medication to be inserted into container 210 to fill a prescription, a size and/or shape of the medication, a frequency at which the medication is to be taken (e.g., every 12 hours, every 24 hours, etc.), pharmacy information (e.g., a pharmacy name, a pharmacy phone number, a pharmacy email address, etc.), special instructions (e.g., take the medication with food), or the like.

Container 210 may store the authentication information and the prescription information in a memory included in container 210.

As further shown in FIG. 6, process 600 may include unlocking a lockable lid based on the received authentication information and the configured authentication information (block 630). For example, container 210 may unlock the lockable lid.

Container 210 may compare the received authentication information with the configured authentication information. If the received authentication information does not match the stored authentication information, then container 210 may determine that the user is not authorized to unlock the lockable lid and may keep the lockable lid locked.

If the received authentication information matches the configured authentication information, then container 210 may unlock the lockable lid. In some implementations, a processor included in container 210 may send a signal to the lockable lid instructing the lockable lid to unlock. The lockable lid may receive the signal and unlock based on the signal.

In some implementations, the lockable lid (e.g., lockable lid 418 and/or lockable lid 512) may include a key hole and a manual lock. The user may insert a key into the keyhole and unlock the lockable lid.

As further shown in FIG. 6, process 600 may include receiving medication associated with the prescription information (block 640). For example, the user may open the unlocked lockable lid and insert medication (e.g., pills, liquid, cream, etc.) into a secure chamber (e.g., secure chamber 420 and/or secure chamber 524) included in container 210.

The user may insert the entire amount of medication required to fill a prescription associated with the prescription information into secure chamber 524. For example, the user may insert a day's worth, week's worth, and/or a month's worth of medication into the secure chamber.

As further shown in FIG. 6, process 600 may include locking the lockable lid included in container 210 (block 650). For example, the user may close the lockable lid and container 210 may lock the lockable lid preventing access to the medication held by the secure chamber.

As further shown in FIG. 6, process 600 may include configuring a dispensing device included in container 210 based on the prescription information (block 660). For example, container 210 may configure a dispensing device (e.g., dispenser 422 and/or pump 514) to dispense a particular amount of medication at any one time based on the prescription information.

In the case of pill container 400 (e.g., container 210), pill container 400 may adjust the size and/or shape of an opening of dispenser 422 based on the size and/or shape of the medication (e.g., a pill) indicated by the prescription information. For example, a processor included in pill container 400 may send a signal to dispenser 422 to change the size and/or shape of the rim surrounding the opening to change the size and/or shape of the opening.

In the case of fluid container 500 (e.g., container 210), fluid container 500 may adjust the amount of fluid pumped through pump 514. For example, a processor included in fluid container 500 may send a signal to pump 514 to change the amount of fluid dispensed by pump 514.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

FIG. 7 is a flow chart of an example process 700 for dispensing medication held by container 210. In some implementations, one or more process blocks of FIG. 7 may be performed by container 210. In some implementations, one or more process blocks of FIG. 7 may be performed by another device or a group of devices separate from or including container 210, such as user device 220, and/or server device 230.

As shown in FIG. 7, process 700 may include determining a dispense time based on the prescription information and a previous dispense time (block 710). For example, container 210 may determine the dispense time. The dispense time may represent a next or subsequent time to dispense medication from container 210.

The prescription information may indicate a frequency at which the medication is to be taken by a patient (e.g., every 12 hours, every 24 hours, etc.). The previous dispense time may indicate the most recent time that medication was dispensed by container 210 and/or should have been dispensed from container 210 (e.g., if a user misses a dose of medication). Container 210 may determine the dispense time by adding a length of time indicated by the frequency (e.g., 12 hours, 24 hours, etc.) to the previous dispense time. For example, assume the medication is to be taken every 8 hours and the previous dispense time was 1:00 PM. Accordingly, the time to dispense medication would be 8 hours later at 9:00 PM.

As further shown in FIG. 7, process 700 may include determining a quantity of medication to dispense at the dispense time based on the prescription information (block 720). For example, container 210 may determine a quantity of medication to dispense at the dispense time.

The prescription information may indicate a dosage of the medication (e.g., a quantity of pills, a quantity of fluid, etc.). Additionally, or alternatively, the prescription information may indicate what happens if the patient misses a dose of medication (e.g., container 210 does not dispense the medication at the dispense time and/or during a range around the dispense time). In some implementations, the prescription information may indicate that the patient should take two doses of the medication at the dispense time if the previous dose was missed. In some implementations, the prescription information may indicate that the patient should skip the missed dose and should take a single dose of the medication at the dispense time. Thus, container 210 may determine a quantity of medication or a number of doses of medication that should be dispensed at the dispense time.

Container 210 may determine a quantity of medication to dispense (e.g., a number of pills, a volume of fluid, etc.) based on the dosage of the medication and a number of doses to be dispensed at the dispense time.

As further shown in FIG. 7, process 700 may include dispensing the quantity of medication from a secure chamber included in container 210 at the dispense time (block 730). For example, container 210 may dispense the quantity of medication at the dispense time.

In some implementations, container 210 may output an alert at the dispense time indicating that it is time to dispense medication. For example, a display (e.g., display 404 and/or display 504) may display a message indicating that it is time to dispense medication, an indicator light (e.g., indicator light 406 and/or indicator light 506) may output a light, and/or a speaker (e.g., speaker 408 and/or speaker 508) may output a sound.

In some implementations, a user (e.g., a patient) may input a request to container 210 for container 210 to dispense the medication. For example, the user may press a button (e.g., button 410 and/or button 510) and/or touch a touchscreen included in container 210 to request the medication be dispensed. Container 210 may determine whether the present time (e.g., a time the request is input) matches the dispense time (e.g., a particular range of time around the dispense time). If the present time does not match the dispense time, container 210 may not dispense the quantity of medication determined to be dispensed at the dispense time. Container 210 may output an alert via the display, the indicator light, and/or the speaker indicating that the medication will not be dispensed at the present time. If the present time matches the dispense time, container 210 may dispense the quantity of medication determined to be dispensed at the dispense time.

When container 210 takes the form of pill container 400, pill container 400 may dispense one or more pills by causing dispenser 422 to dispense the one or more pills from secure chamber 420 into dispensing chamber 426. In some implementations, pill container 400 may automatically dispense the pill at the dispense time and may not wait for a user to input a request to dispense the pill.

Dispenser 422 may dispense one pill at a time and keep dispensing pills until the quantity of pills, determined to be dispensed, has been dispensed. Pill container 400 may determine a quantity of pills that has been dispensed from dispenser 422 based on a weight measured by scale 414 and a weight of a pill. For example, a pill dispensed by dispenser 422 may fall to the bottom of dispensing chamber 426 and rest on top of scale 414. The prescription information stored by pill container 400 may indicate the weight of a pill. Pill container 400 may determine a weight of the quantity of pills to be dispenses at the dispense time based on the weight of a pill and the quantity of pills to be dispensed. Scale 414 may determine when a weight measured by the scale changes by the weight of the quantity of pills determined to be dispensed at the dispense time and send a signal to dispenser 422 to stop dispensing pills. Dispenser 422 may continue dispensing pills until dispenser 422 receives a signal to stop. In some implementations, pill container 400 may store a record indicating the quantity of pills dispensed and a time that the quantity of pills was dispensed. In some implementations, dispenser 422 may track the quantity of pills dispensed and scale 414 may be used to check that dispenser 422 dispensed the correct quantity of pills.

The user may open outer lid 412 and remove the pill(s) from dispensing chamber 426. The user may close outer lid 412 after the pill(s) has/have been removed.

When container 210 takes the form of fluid container 500, fluid container 500 may dispense medication by causing pump 514 to pump medication out of nozzle 516. In some implementations, a user may press button 510 and pump 514 may automatically dispense the quantity of medication all at one time (e.g., one pump of pump 514). Additionally, or alternatively, pump 514 may dispense the quantity of medication over multiple pumps of pump 514. For example, a user may prefer to pump out a first portion of the quantity of medication, administer the first portion, pump out a second portion of the quantity of medication, and administer the second portion rather than pump out the entire quantity of medication at one time and have to administer all the medication at the same time. For instance, pump 514 may allow a user to dispense partial doses of the medication (up to the allowed dose of medication) and allow the user to dispense any remaining parts of a dose of medication at a later time.

In some implementations, a user may hold down button 510 and pump 514 may dispense a portion of the medication while button 510 is held down. The user may release button 510 before the entire quantity of medication that is supposed to be dispensed at the dispense time has been dispensed. Sensor 520 may detect a quantity of the portion dispensed. The user may hold down button 510 again and pump 514 may dispense another portion of the medication. This process may be repeated until the portions of the medication dispensed (e.g., sensed by sensor 530) matches the quantity of medication that is supposed to be dispensed at the dispense time. Indicator light 506 may display a first color (e.g., green) when the entire quantity of medication has not been dispensed, and may display a second color (e.g., red) when the entire quantity of medication has been dispensed. Display 504 and/or speaker 510 may output similar indicators. When the medication dispensed (e.g., sensed by sensor 530) matches the quantity of medication that is supposed to be dispensed at the dispense time, fluid container 500 may cause pump 514 to stop dispensing medication until a next dispense time. Additionally, or alternatively, if the medication dispensed is less than the quantity of medication that is supposed to be dispensed at the dispense time, fluid container 500 may allow a remaining amount of medication to be carried over and dispensed later (e.g., at another dispense time) depending on the prescription information.

As further shown in FIG. 7, process 700 may include determining whether the dispensed quantity of medication has been removed from container 210 (block 740). For example, container 210 may determine whether the dispensed medication has been removed.

In some implementations, pill container 400 (e.g., container 210) may determine if a dispensed pill has been removed from dispensing chamber 426 based on a weight measured by scale 414. For example, if scale 414 detected the weight of a pill at one time and then scale 414 detects the measured weight decreases by the weight of the pill, pill container 400 may determine that the pill has been removed from dispensing chamber 426. On the other hand, if the weight measured by the scale does not decrease by the weight of the pill, pill container 400 may determine the pill is still inside dispensing chamber 426.

In some implementations, fluid container 500 (e.g., container 210) may dispense the medication out of nozzle 516 and outside of fluid container 500 (e.g., in a cup, in a user's hand, etc.). In such cases, fluid container 500 may not determine whether the dispensed medication has been removed from fluid container 500 or always determine the dispensed medication has been removed from fluid container 500. However, as previously discussed, fluid container 500 may include an upper dispensing chamber above lockable lid 512, and nozzle 516 may dispense the medication into the upper dispensing chamber. The upper dispensing chamber may include a scale that detects whether a dose of medication has been dispensed into the upper dispensing chamber and/or whether the dispensed medication has been removed from the upper dispensing chamber.

In some implementations, container 210 may output information via a display, an indicator light, and/or a speaker indicating whether the medication has been removed from container 210 and/or remains in container 210.

In some implementations, container 210 may record and store a time at which the medication was removed from container 210. Container 210 may update the dispense time based on the time at which the medication was removed from container 210 and/or the time at which the medication was dispensed from container 210. For example, if the medication has not been removed from container 210, container 210 may determine that another dose of medication does not need to be dispensed at least until the previously dispensed medication has been removed from container 210.

As further shown in FIG. 7, process 700 may include determining a remaining quantity of medication in the secure chamber (block 750). For example, container 210 may determine the remaining quantity of medication in the secure chamber.

In some implementations, pill container 400 (e.g., container 210) may determine the remaining quantity of medication in secure chamber 420 based on the prescription information and a number of doses of medication dispensed by pill container 400. For example, the prescription information may indicate a quantity of total pills inserted into secure chamber 420 to fill a prescription. Pill container 400 may record how many pills have been dispensed as the pills are dispensed using scale 414 as previously discussed. Pill container 400 may subtract the pills that have been dispensed from the pills inserted into secure chamber 420 to determine the quantity of pills remaining in secure chamber 420.

Additionally, or alternatively, pill container 400 may include another scale 414 at the bottom of secure chamber 420. The other scale 414 may measure a weight of the remaining pills in secure chamber 420. The weight of the remaining pills may be divided by a weight of a pill (as indicated by the prescription information) to determine the quantity of pills remaining in secure chamber 420. Furthermore, the other scale 414 may be used to determine whether a pill was dispensed from secure chamber 420 at block 730 based on whether the measured weight of the remaining pills decreases by a pill weight.

In some implementations, fluid container 500 (e.g., container 210) may determine a remaining quantity of medication inside secure chamber 524 based on the prescription information and medication level sensed by rod 526 and float 528. Fluid container 500 may determine a volume of medication remaining in secure chamber 524 based on rod 526 and float 528. The volume of medication may be divided by a dosage volume (as indicated by the prescription information) to determine the remaining doses of medication inside secure chamber 524.

Additionally, or alternatively, fluid container 500 may include a scale at the bottom of secure chamber 524 that measures a weight of the remaining medication in secure chamber 524. The weight of the remaining medication may be divided by a weight of a dose (as indicated by the prescription information) to determine the quantity of doses remaining in secure chamber 524.

In some implementations, fluid container 500 may determine the remaining quantity of medication in secure chamber 524 based on the prescription information and a number of doses of medication dispensed by fluid container 500. For example, the prescription information may indicate a quantity of total doses of medication inserted into secure chamber 524 to fill a prescription. Fluid container 500 may record how many doses have been dispensed using sensor 520 as previously discussed. Fluid container 500 may subtract the doses of medication that have been dispensed from the doses of medication inserted into secure chamber 524 to determine the quantity of doses remaining in secure chamber 524.

Container 210 may store information indicating the quantity of medication remaining in secure chamber 524. In some implementations, container 210 may output information indicating how much medication remains in the secure chamber included in container 210. For example, a display may display a number of doses remaining and/or an indicator light may display a different color and/or flash when a threshold quantity of doses remain in the secure chamber.

As further shown in FIG. 7, process 700 may include providing a message to server device 230 based on the remaining quantity of medication and/or a detected problem (block 760). For example, container 210 may send a message to server device 230.

Container 210 may send a message to server device 230 indicating the quantity of medication remaining in a secure chamber. In some implementations, container 210 may automatically request a refill be ordered based on the quantity of medication remaining and the prescription information. For example, the prescription information may identify a pharmacy where a prescription may be refilled.

In some implementations, container 210 may detect a problem. For example, container 210 may detect that no medication is being dispensed at dispensing times, dispensed medication is not being removed from container 210 at appropriate times, and/or there is a malfunction with a part of container 210. Container 210 may send a message to server device 230 indicating the problem.

In some implementations, container 210 may unlock a lockable lid that covers a secure chamber if medication is not being dispensed properly. Accordingly, a user (e.g., a patient) may be given access to the medication in the secure chamber so that the user is not deprived of the medication due to an error caused by container 210. Additionally, or alternatively, server device 230 may send a command to container 210 to unlock the lockable lid. Container 210 may receive the command and unlock the lockable lid based on the command.

In some implementations, process 700 may return to block 710 to determine a dispense time for another dose of the medication.

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 8A:
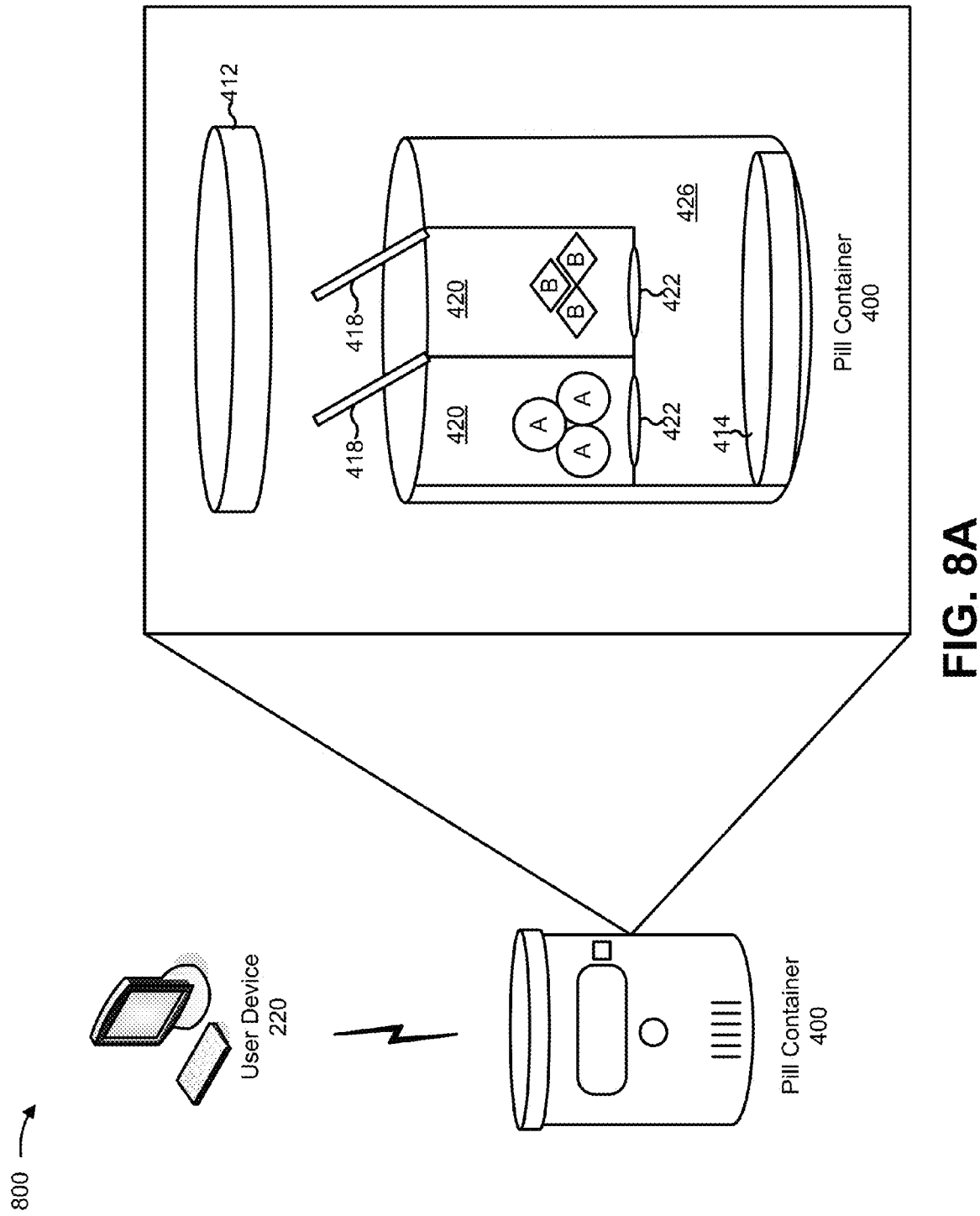
FIGS. 8A and 8B are diagrams of an example implementation relating to the example processes shown in FIGS. 6 and 7.
Figure 8B:
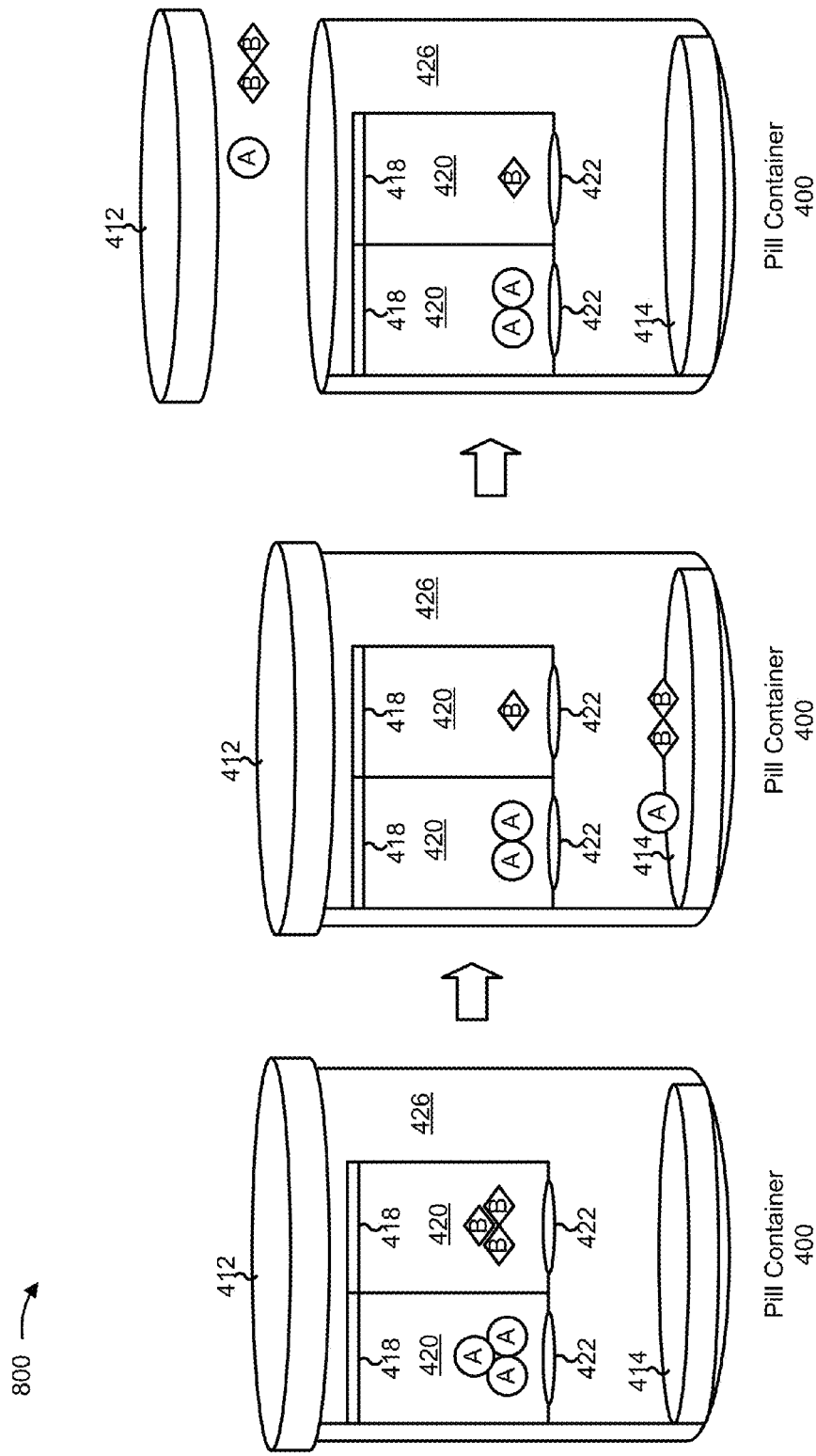

FIGS. 8A and 8B are diagrams of an example implementation 800 relating to example processes 600 and 700 shown in FIGS. 6 and 7. FIGS. 8A and 8B show an example of inserting medication into pill container 400 and dispensing medication held by pill container 400.

In example implementation 800, assume a pharmacist operates user device 220 and inputs authentication information and prescription information into user device 220. Further, assume the prescription information indicates prescriptions for medication A and medication B. Also, assume the prescription information indicates one pill of medication A and two pills of medication B should be dispensed at a dispense time. Furthermore, assume the prescription information indicates a size, a shape, and a weight of a pill of medication A and a pill of medication B.

As shown in FIG. 8A, user device 220 may send the authentication information and the prescription information to pill container 400 via a RF communication. Pill container 400 may receive and store the authentication information and the prescription information. Assume pill container 400 changes the size and shape of the opening in dispensers 422 based on the prescription information. Pill container 400 may unlock lockable lids 418 based on the authentication information. The pharmacist may open outer lid 412 and lockable lids 418, and add medication A pills to a first secure chamber 420 and a medication B pills to a second secure chamber 420 to fill the prescriptions associated with the prescription information. The pharmacist may close outer lid 412 and lockable lids 418. Pill container 400 may lock lockable lids 418. The pharmacist may give pill container 400 to a patient.

In FIG. 8B, assume the patient pushes button 410 to dispense medication at the dispense time indicated by the prescription information. Dispensers 422 may dispense one medication A pill and two medication B pills from secure chambers 420 into dispensing chamber 426 based on the prescription information. Scale 414 may detect that one medication A pill has been dispensed and two mediation B pills have been dispensed based on the weight of the dispensed pills and the prescription information. Scale 414 may send a signal to dispensers 422 to stop dispensing pills. The patient may open outer lid 412 and remove the dispensed pills.

As indicated above, FIGS. 8A and 8B are provided merely as an example. Other examples are possible and may differ from what was described with regard to FIGS. 8A and 8B.

Figure 9A:
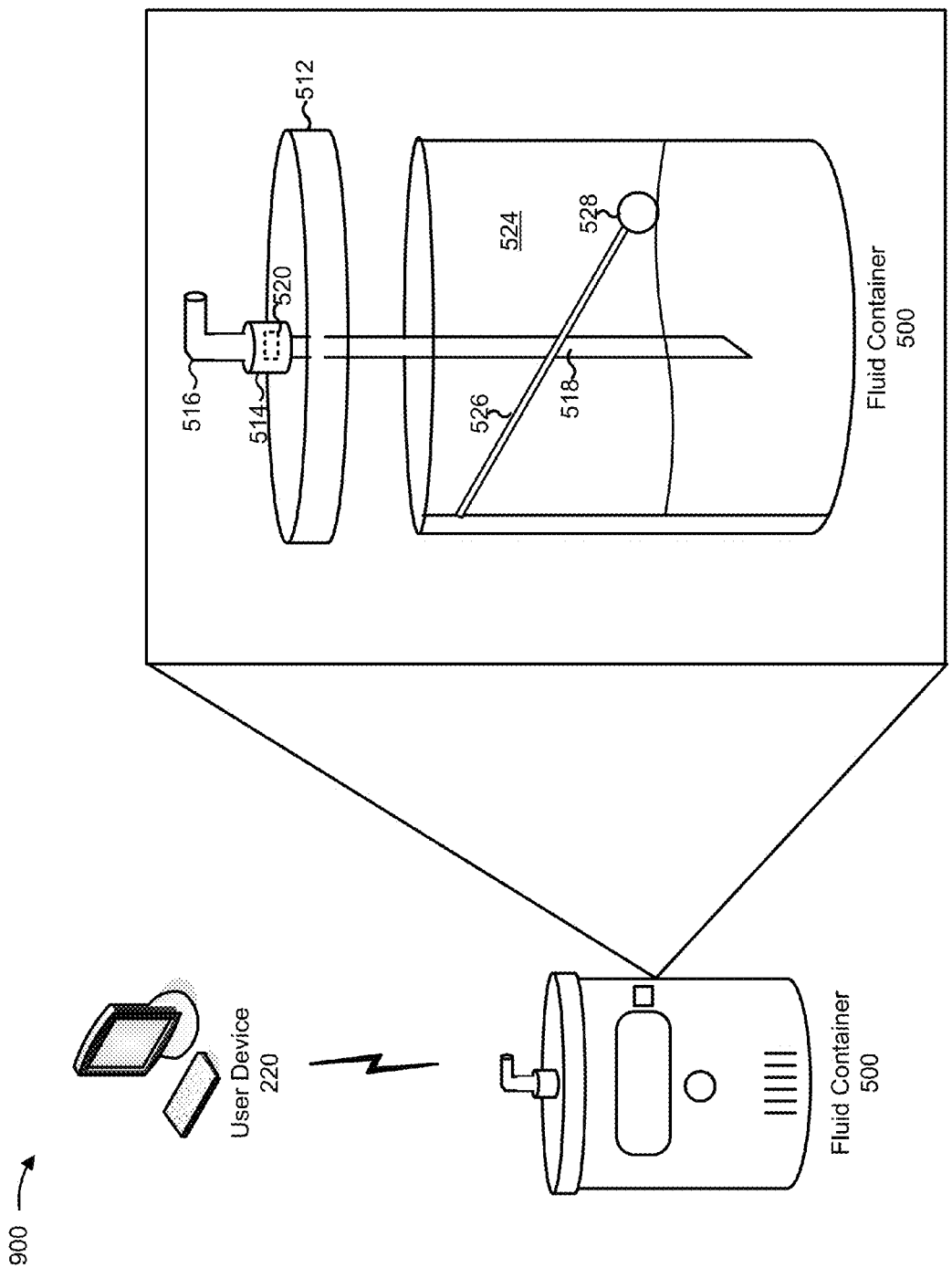
FIGS. 9A and 9B are diagrams of an example implementation relating to the example processes shown in FIGS. 6 and 7.
Figure 9B:
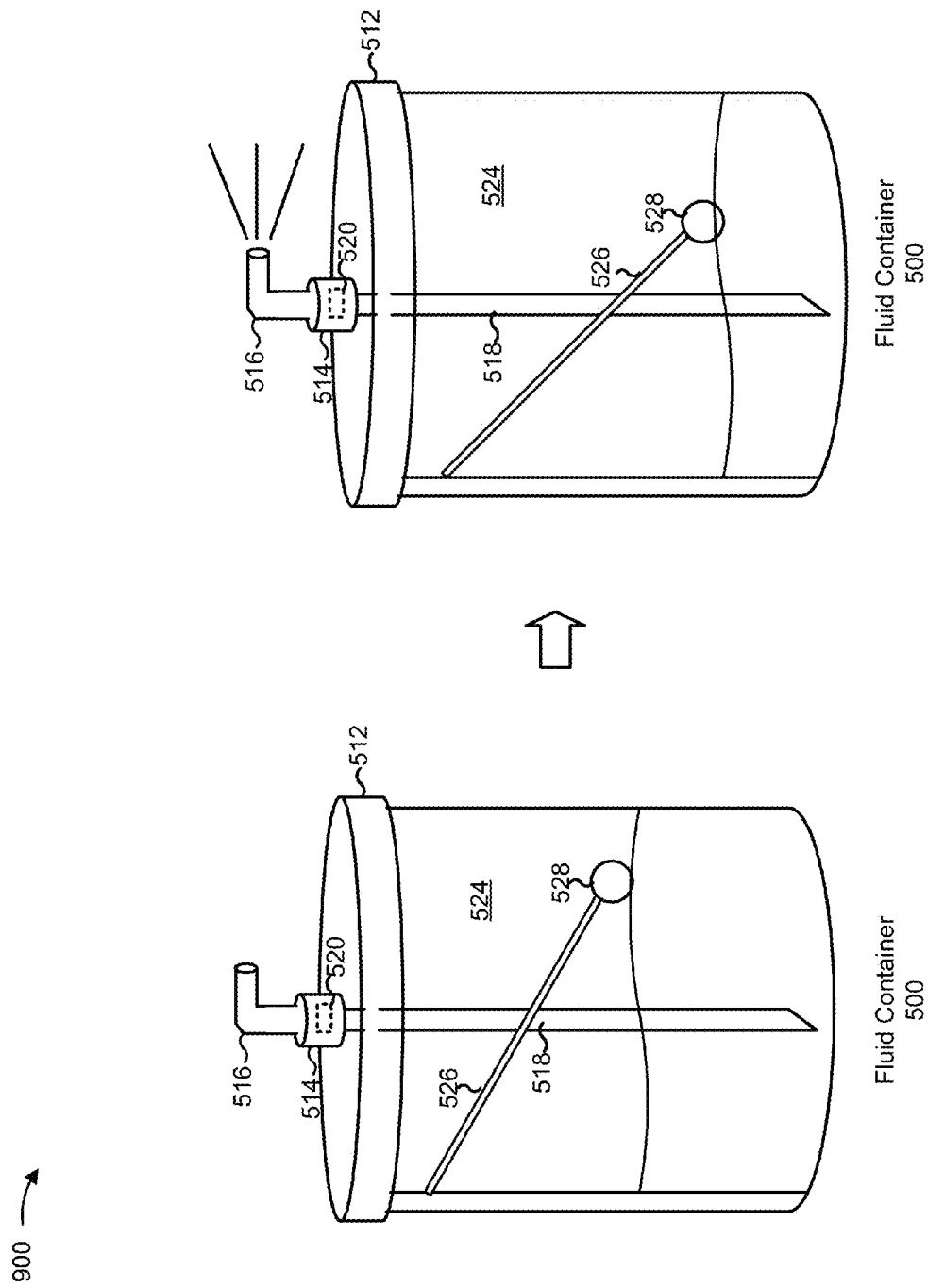

FIGS. 9A and 9B are diagrams of an example implementation 800 relating to example processes 600 and 700 shown in FIGS. 6 and 7. FIGS. 9A and 9B show an example of inserting medication into fluid container 500 and dispensing medication held by fluid container 500.

In example implementation 900, assume a pharmacist operates user device 220 and inputs authentication information and prescription information into user device 220. Further, assume the prescription information indicates a total of 15 milliliters (ml) of medication are to be inserted into fluid container 500. Also, assume the prescription information indicates 0.5 ml of medication should dispensed at a dispense time.

As shown in FIG. 9A, user device 220 may send the authentication information and the prescription information to fluid container 500 via a RF communication. Fluid container 500 may receive and store the authentication information and the prescription information. Fluid container 500 may adjust pump 514 to dispense 0.5 ml of medication at a time based on the prescription information. Fluid container 500 may unlock lockable lid 512 based on the authentication information. The pharmacist may open lockable lid 512 and add 15 ml of medication to secure chamber 524 to fill the prescription associated with the prescription information. The pharmacist may close lockable lid 512. Fluid container 500 may lock lockable lid 512 and the pharmacist may give fluid container 500 to a patient.

In FIG. 9B, assume the patient pushes button 510 to dispense medication at the dispense time indicated by the prescription information. Pump 514 may dispense 0.5 ml of medication out of nozzle 516. Rod 526 and float 528 may detect the change in medication remaining in secure chamber 524, and fluid container 500 may display information indicating 14.5 ml and/or 29 doses of medication remain in fluid container 500. Additionally, or alternatively, if pump 514 dispenses less than 0.5 ml of medication, fluid container 500 may display an amount of medication that may still be dispensed for the dose. For example, if only 0.3 ml have been dispensed by fluid container 500, fluid container 500 may display information indicating that 0.2 ml may still be dispensed for the current dose.

As indicated above, FIGS. 9A and 9B are provided merely as an example. Other examples are possible and may differ from what was described with regard to FIGS. 9A and 9B.

Implementations described herein provide a container that may dispense a medication at prescribed times. Additionally, implementations described herein may provide a container that dispenses an accurate amount of medication. Accordingly, the container may help a patient take a prescribed dosage of medication at a prescribed time.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

To the extent the aforementioned implementations collect, store, or employ personal information provided by individuals, it should be understood that such information shall be used in accordance with all applicable laws concerning protection of personal information. Storage and use of personal information may be in an appropriately secure manner reflective of the type of information, for example, through various encryption and anonymization techniques for particularly sensitive information.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items, and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A container, comprising:
   a secure chamber to hold a medication;
   a lockable lid covering an opening of the secure chamber;
   a dispensing device;
   a scale; and
   one or more processors to:
      receive prescription information indicating a frequency to dispense the medication and indicating a dose of the medication to dispense at a dispense time;
      determine the dispense time based on the frequency to dispense the medication, the dispense time being a time to dispense a dose of the medication;
      cause the dispensing device to dispense the dose of the medication from the secure chamber at the dispense time;
      measure, using the scale, a weight of the dose of the medication that is dispensed;
      cause the dispensing device to stop dispensing the medication based on the weight that is measured;
      detect that the container has failed to dispense another dose of the medication at a subsequent dispense time while the secure chamber holds the medication; and
      unlock the lockable lid based on the container failing to dispense the other dose of the medication at the subsequent dispense time.

2. The container of claim 1, further comprising:
   a dispensing chamber separate from the secure chamber;
   where the one or more processors, when causing the dispensing device to dispense the dose of the medication, are to:
      cause the dispensing device to dispense the dose of the medication from the secure chamber into the dispensing chamber for removal from the container.

3. The container of claim 2, where the scale is positioned at a bottom surface of the dispensing chamber, and
   where the one or more processors, when measuring the weight, are to measure the weight of the dose of the medication dispensed into the dispensing chamber.

4. The container of claim 2, where the one or more processors are further to:
   determine a time that the dose of the medication was removed from the container based on a second weight measured by the scale indicating the dose of the medication has been removed from the dispensing chamber; and
   update the dispense time based on the time the dose of the medication was removed from the dispensing chamber.

5. The container of claim 1, where the medication includes a pill and the prescription information indicates at least one of a size or a shape of the pill, and
   where the one or more processors are further to:
      adjust at least one of a size or a shape of a rim included in the dispensing device, based on at least one of the size or the shape of the pill, to change a size or a shape of an opening the pill is dispensed through.

6. The container of claim 1, further comprising:
   a plurality of secure chambers associated with a plurality of respective dispensing devices,
      the plurality of secure chambers including the secure chamber, and
      the plurality of respective dispensing devices including the dispensing device.

7. The container of claim 1, where the dispensing device is configured to dispense a pill, and
   where the medication includes at least one pill.

8. The container of claim 1, where the dispensing device includes a pump to dispense a fluid, and
   where the medication includes a fluid.

9. A computer-readable medium storing instructions, the instructions comprising:
   one or more instructions that, when executed by one or more processors, cause the one or more processors to:
      receive prescription information indicating a frequency to dispense a dose of a medication;
      determine a dispense time based on the frequency to dispense the dose of the medication,
         the dispense time being a time to dispense the dose of the medication;
      cause a dispensing device of a container to start dispensing the medication held by a secure chamber of the container at the dispense time;
      detect, using a sensor, a quantity of dispensed medication;
      determine the dose of the medication has been dispensed based on determining that the detected quantity of dispensed medication matches the dose of the medication;
      cause the dispensing device to stop dispensing the medication held by the secure chamber based on the dose of the medication having been dispensed;
      detect that the container has failed to dispense another dose of the medication at a subsequent dispense time while the secure chamber holds the medication; and
      unlock a lockable lid, which covers an opening of the secure chamber, based on the container failing to dispense the other dose of the medication at the subsequent dispense time.

10. The computer-readable medium of claim 9, where the one or more instructions, when executed by the one or more processors, further cause the one or more processors to:
 determine a quantity of the medication held by the secure chamber based on information sensed by the sensor; and
 display information indicating the quantity of the medication held by the secure chamber.

11. The computer-readable medium of claim 10, where the prescription information indicates an initial quantity of the medication held by the secure chamber, and
 where the one or more instructions, that cause the one or more processors to determine the quantity of the medication held by the secure chamber, cause the one or more processors to:
  store, in a memory, dispense information each time the dose of the medication is dispensed;
  determine a total dispensed quantity of the medication based on the dispense information; and
  determine the quantity of the medication held by the secure chamber based on the initial quantity of the medication held by the secure chamber and the total dispensed quantity of the medication.

12. The computer-readable medium of claim 10, where the sensor includes a scale and the prescription information indicates a weight of a dose of the medication, and
 where the one or more instructions, that cause the one or more processors to determine the quantity of the medication held by the secure chamber, cause the one or more processors to:
  measure a weight of the medication held by the secure chamber using the scale; and
  determine a quantity of doses of the medication held by the secure chamber based on the weight of the medication held by the secure chamber and the weight of the dose of the medication.

13. The computer-readable medium of claim 10, where the prescription information indicates a volume of a dose of the medication, and
 where the one or more instructions, that cause the one or more processors to determine the quantity of the medication held by the secure chamber, cause the one or more processors to:
  measure a volume of the medication held by the secure chamber using the sensor; and
  determine a quantity of doses of the medication held by the secure chamber based on the volume of the medication held by the secure chamber and the volume of the dose of the medication.

14. The computer-readable medium of claim 9, where the one or more instructions, when executed by the one or more processors, further cause the one or more processors to:
 receive authentication information for unlocking a lockable lid via a communication interface or an input component,
  the lockable lid covering an opening of the secure chamber;
 unlock the lockable lid based on the authentication information; and
 lock the lockable lid before causing the dispensing device to dispense the dose of the medication.

15. A method, comprising:
 locking, by a container, a lockable lid that covers an opening of a secure chamber holding a medication;
 receiving, by the container, prescription information indicating a frequency to dispense the medication and indicating a dose of the medication to dispense at a dispense time;
 determining, by the container, the dispense time based on the frequency to dispense the medication,
  the dispense time being a time to dispense the dose of the medication;
 dispensing, by the container, the dose of the medication from the secure chamber at the dispense time;
 detecting, by the container, that the container has failed to dispense another dose of the medication at a subsequent dispense time while the secure chamber holds the medication; and
 unlocking, by the container, the lockable lid based on the container failing to dispense the other dose of the medication at the subsequent dispense time.

16. The method of claim 15, further comprising:
 adjusting an amount of fluid that may be pumped through a pump based on the prescription information, and
 where dispensing the dose of the medication includes dispensing the dose of the medication through the pump.

17. The method of claim 15, where dispensing the dose of the medication includes dispensing the dose of the medication through a pump and out of the container, the method further comprising:
 dispensing a plurality of portions of the dose of the medication at different times based on user input;
 sensing an amount of the medication dispensed through the pump; and
 stopping the medication from being dispensed through the pump when the amount of the medication dispensed through the pump equals the dose of the medication.

18. The method of claim 15, further comprising:
 determining a quantity of medication remaining in the container based on at least one of a weight or a volume of the medication in the container after dispensing the dose of the medication;
 outputting information indicating the quantity of medication remaining in the container,
  where outputting the information includes sending the information indicating the quantity of medication remaining in the container to a server via a communication interface included in the container.

19. The method of claim 15, further comprising:
 detecting that a dispensed dose of medication has not been removed from the container based on detecting the dispensed dose of medication inside the container after being dispensed from the secure chamber; and
 waiting to dispense another dose of medication until after the dispensed dose of medication has been removed from the container.

20. The method of claim 15, further comprising:
 sending a message to a server device based on detecting that the container has failed to dispense the other dose of the medication;
 receiving a command from the server device to unlock the lockable lid based on the message; and
 where unlocking the lockable lid includes unlocking the lockable lid based on the command from the server device.

* * * * *